(12) United States Patent
Liu et al.

(10) Patent No.: US 12,285,187 B2
(45) Date of Patent: Apr. 29, 2025

(54) REUSABLE ULTRASONIC SCALPEL

(71) Applicant: INNOLCON MEDICAL TECHNOLOGY (SUZHOU) CO., LTD., Jiangsu (CN)

(72) Inventors: Ke Liu, Jiangsu (CN); Xiaohe Yuan, Jiangsu (CN); Zhenzhong Liu, Jiangsu (CN); Zhongyu Yan, Irvine, CA (US); Wei Luo, Jiangsu (CN)

(73) Assignee: Innolcon Medical Technology (Suzhou) Co., Ltd., Jiangsu (CN)

( * ) Notice: Subject to any disclaimer, the term of this patent is extended or adjusted under 35 U.S.C. 154(b) by 414 days.

(21) Appl. No.: 17/635,195

(22) PCT Filed: Apr. 13, 2020

(86) PCT No.: PCT/CN2020/084408
§ 371 (c)(1),
(2) Date: Feb. 14, 2022

(87) PCT Pub. No.: WO2021/027302
PCT Pub. Date: Feb. 18, 2021

(65) Prior Publication Data
US 2022/0287736 A1    Sep. 15, 2022

(30) Foreign Application Priority Data

Aug. 15, 2019  (CN) .......................... 201910752035.3

(51) Int. Cl.
*A61B 17/32*      (2006.01)
*A61B 17/295*     (2006.01)
(Continued)

(52) U.S. Cl.
CPC .... *A61B 17/320092* (2013.01); *A61B 17/295* (2013.01); *A61B 17/32002* (2013.01);
(Continued)

(58) Field of Classification Search
None
See application file for complete search history.

(56) References Cited

U.S. PATENT DOCUMENTS

| 5,346,502 A | 9/1994 | Estabrook et al. |
| 2007/0282332 A1 | 12/2007 | Witt et al. |

(Continued)

FOREIGN PATENT DOCUMENTS

| CN | 104783868 A | 7/2015 |
| CN | 108354652 A | 8/2018 |

(Continued)

*Primary Examiner* — Elizabeth Houston
*Assistant Examiner* — Jonathan A Hollm
(74) *Attorney, Agent, or Firm* — Seed IP Law Group LLP

(57) ABSTRACT

A reusable ultrasonic scalpel comprising a handle assembly and an ultrasonic waveguide extended to the distal end transmitting ultrasonic mechanical energy. Outside the ultrasonic waveguide is a sheath assembly, and the sheath assembly is detachably connected to the handle assembly by a quick connecting mechanism. The beneficial effects are mainly reflected on: reliable installation, easy to disassemble, easy to clean and disinfect. The sheath assembly serving as a consumable may be quickly replaced, while the remaining parts may be reused, and may undergo cleaning and high temperature steam sterilization. Thus, the cost of surgical consumables is greatly reduced, the burden on patients is reduced, and the risk of cross-infection when using the ultrasonic scalpel bar is also reduced.

11 Claims, 12 Drawing Sheets

(51) Int. Cl.
*A61B 17/3211* (2006.01)
*A61B 17/00* (2006.01)

(52) U.S. Cl.
CPC ... *A61B 17/3211* (2013.01); *A61B 2017/0046* (2013.01); *A61B 2017/320082* (2017.08); *A61B 2017/320094* (2017.08)

(56) References Cited

U.S. PATENT DOCUMENTS

| | | |
|---|---|---|
| 2008/0234708 A1 | 9/2008 | Houser et al. |
| 2012/0116396 A1* | 5/2012 | Price .................... H02J 7/0044 606/45 |
| 2017/0105753 A1 | 4/2017 | Conlon et al. |
| 2018/0360486 A1* | 12/2018 | Beaupre ......... A61B 17/320068 |
| 2020/0046367 A1* | 2/2020 | Baril ................. A61B 17/1285 |

FOREIGN PATENT DOCUMENTS

| | | | |
|---|---|---|---|
| CN | 108969058 | A | 12/2018 |
| CN | 109009330 | A | 12/2018 |
| CN | 110448357 | A | 11/2019 |
| EP | 2635220 | A1 | 9/2013 |
| EP | 3386371 | A1 | 10/2018 |
| WO | 2011100321 | A2 | 8/2011 |
| WO | WO 2012061645 | A1 | 5/2012 |
| WO | WO 2017100412 | A1 | 6/2017 |
| WO | WO 2018232226 | A1 | 12/2018 |
| WO | WO 2019015502 | A1 | 1/2019 |

\* cited by examiner

REUSABLE ULTRASONIC SCALPEL

BACKGROUND

Technical Field

The present invention relates to medical device field, in particular to an ultrasonic scalpel.

Description of the Related Art

The ultrasonic scalpel refers to a surgical device that amplifies the ultrasonic vibration obtained by the piezoelectric transducer (Ultrasonic generator transfers electric energy to the piezoelectric transducer, and the transducer converts the electric energy to ultrasonic mechanical energy), through the amplified vibration at the scalpel blade, it is used for soft tissue cutting and coagulation. Clinical use of this device allows lesions to be removed at lower temperature and with less bleeding, and ensures minimal lateral tissue thermal damage. With the wide use of minimally invasive surgery, ultrasonic scalpel has become a conventional surgical instrument.

In general, ultrasonic scalpel includes transducer, handle, and waveguide assembly extended from the distal end of the handle. The waveguide assembly of the existing ultrasonic scalpel usually includes an ultrasonic waveguide, an inner sheath and an outer sheath. The inner sheath is located between the waveguide and the outer sheath, and movable in a certain range along the axis, thus to open or close the active clamp with respect to the blade at the distal end of the waveguide assembly, so to achieve the target biological tissue clamping and cutting.

However, this ultrasonic scalpel has a disadvantage, that is, the handle housing and the waveguide assembly is non-detachable structure, once detached, cannot be restored. From the structure of the waveguide assembly, the inner sheath and outer sheath are open at the distal end of the waveguide, i.e., at the surgical site. When the waveguide is in stationary, under capillary action, the liquid tissue of the surgical site will penetrate from the end of the sheath opening to the inside of the assembly body, that is, into the gaps between the inner sheath and the outer sheath, and the inner sheath and the waveguide. While the waveguide vibrates, the silicone support ring on the waveguide becomes like a piston that vibrates with the same frequency as the waveguide, and the liquid tissue is forcefully sucked into the gap between the waveguide body and the inner sheath. After disassembly of the used ultrasonic scalpel, the clotting fat sample and blood clotting were observed on the entire waveguide body and the outer wall of the inner sheath near the side of the blade, especially in the entire waveguide body the knotting phenomenon was more serious. After one or even more surgical operations, the structure and performance of the ultrasonic waveguide is still intact, but the inside of the waveguide assembly cannot be thoroughly cleaned and disinfected. Therefore, the above-mentioned ultrasonic scalpel in accordance with the regulation should be only used as a disposable surgical instrument, after the completion of one surgery should be discarded, but its cost is high. It also lurks huge medical risk: in order to obtain financial benefits, some users reuse the ultrasonic scalpel in the next patient after incomplete cleaning and disinfection, the risk of cross-infection is inevitable.

In view of this, Chinese patents CN201410023651.2, CN201810130712.3, CN201810871843.7, CN201811114 966.2 designed a number of replaceable assembly components, but some of these components are mucomplex structures, manufacturing costs are relatively high, and assembly is also inconvenient, such as, the assembly bases of the inner and outer sheaths use metal parts, so that the sheaths need to be formed with tube expanding process and make rotating grooves. The processing efficiency is low and cost high, and some do not prevent reversal rotation, which may cause subtle displacements by the ultrasonic vibrations that affect the precision of surgery.

BRIEF SUMMARY

The present invention provides a reusable ultrasonic scalpel.

The technical scheme of the present invention is:

A reusable ultrasonic scalpel comprises a handle assembly and extended at its distal end an ultrasonic waveguide for transmitting the ultrasonic mechanical energy. Outside of the ultrasonic waveguide is equipped with a sheath assembly, and the sheath assembly is detachably connected to the handle assembly by a quick-connect mechanism.

Preferably, the sheath assembly comprises an inner sheath assembly and an outer sheath assembly attached to each other. The inner sheath assembly comprises an inner sheath and an inner sheath holder fixed at its proximal end. The outer sheath assembly comprises an outer sheath and an outer sheath holder fixed at its proximal end. The inner sheath is located between the ultrasonic waveguide and the outer sheath, and may move a certain distance along the axis, thus to open or close the active clamp, so that the active clamp and the distal end of the waveguide contact or separate. The inner sheath assembly and the outer sheath assembly are fixed rotationally to each other. The outer sheath holder is fixed axially by means of the first quick-connect mechanism to the rotatory knob at the distal end of the handle assembly, while the inner sheath holder is fixed axially by the second fast-connect mechanism to the spring seat which is within the handle assembly as a part of the drive mechanism.

Preferably, the first quick-connect mechanism comprises the first post mounted on the outer perimeter of the proximal end of the outer sheath holder, and the L-slot arranged axially on the rotary knob, which are mated to each other.

Preferably, the second quick-connect mechanism comprises a second post mounted on the outer perimeter of the inner sheath holder, and an L-type hook arranged axially on the spring seat, which are mated to each other.

Preferably, the axial movement distance of the first post in the L-slot is greater than or equal to the axial movement distance of the second post in the L-type hook.

Preferably, the inner circumferential surface of the out sheath holder has a first plane, the outer circumferential surface of the inner sheath holder has a second plane. The outer sheath holder is located over the outer circumstantial area of the inner sheath holder and the first plane and the second plane limit the rotation of the inner sheath assembly from the outer sheath assembly.

Preferably, the tool rotary knob comprises an internal thread, with which a sheath mounting knob with an external thread is connected, and the proximal end of the sheath mounting knob always applies a force to the outer sheath holder, so that the outer sheath holder is fixed between the sheath mounting knob and the tool rotary knob.

Preferably, the distal end face of the outer sheath holder is a step plane, which is compatible with the post at the proximal end of the sheath mounting knob.

Preferably, the attachment between the inner sheath and inner sheath holder are realized by the mold injection molding process or by glue bonding.

Preferably, the attachment between the outer sheath and outer sheath holder are realized by the mold injection molding process or by glue bonding.

Preferably, the handle assembly and the ultrasonic waveguide are made of high temperature-resistant materials respectively.

The beneficial effects are mainly reflected on: reliable installation, easy to disassemble, easy to clean and disinfect. The sheath assemblies as consumables can be rapidly replaced, while the remaining parts can be reused, cleansed and sterilized by a variety of ways, including high temperature steam sterilization. The cost of consumables for surgery is greatly reduced, the burden on patients is reduced, and the risk of cross-infection in ultrasonic scalpel use is reduced.

DETAILED DESCRIPTION

Figure 1:
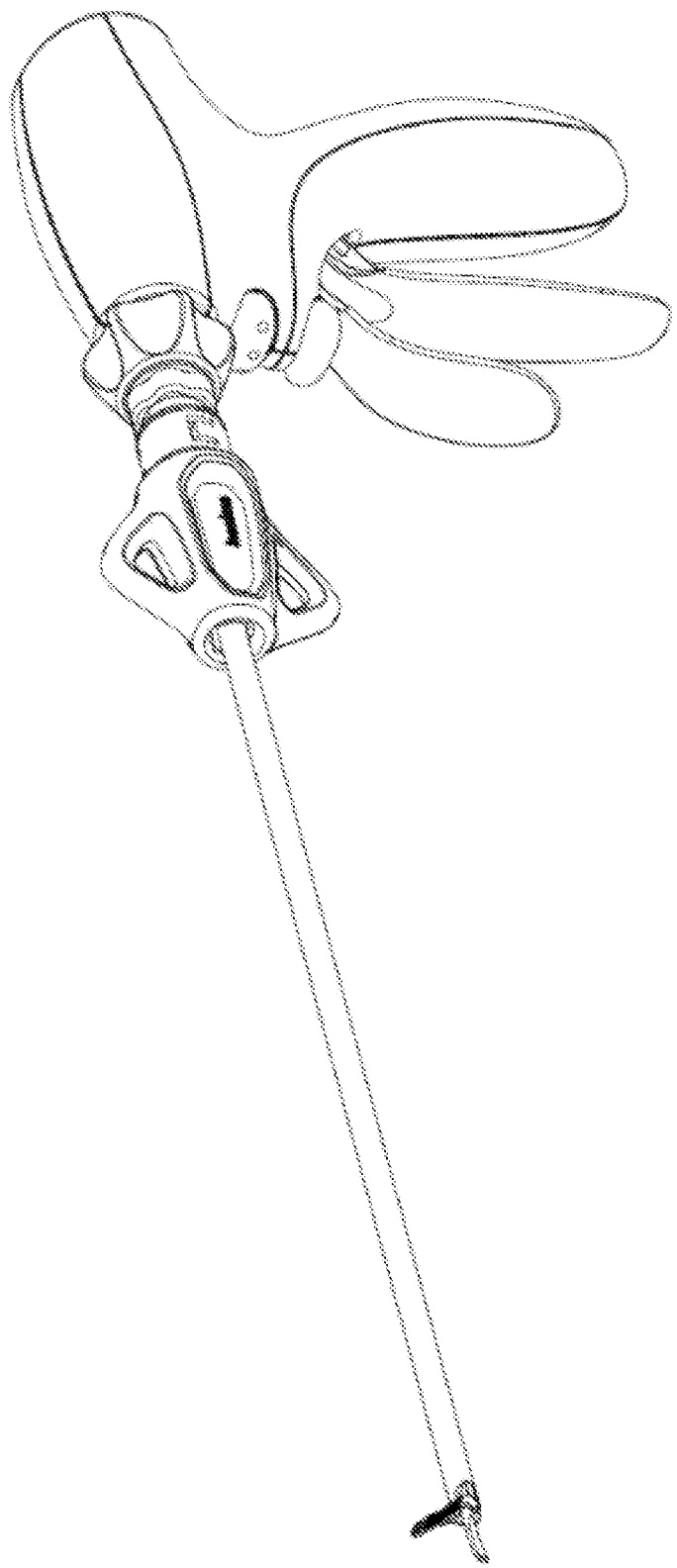
FIG. 1 is a diagram of the ultrasonic scalpel of the present invention.

The following will be combined with the specific embodiment shown in the drawings to describe the present invention in detail. However, these embodiments are not limitations to the present invention; the ordinary technical personnel in the art according to these embodiments making the structure, method, or functional transformation are contained in the scope of protection of the present invention.

In the description of the scheme, it should be noted that the terms "center," "up," "down," "left," "right," "front," "back," "vertical," "horizontal," "inside," "outside" and other indications of the orientation or position relationship based on the drawings, only to facilitate the description and simplification of the description, rather than to indicate or imply that the device or component must have a specific orientation, with a specific orientation structure and operation, and therefore cannot be understood as a limitation of the present invention. In addition, the terms "first," "second," and "third" are used only for descriptive purposes and are not understood to indicate or imply relative importance. Also, in the description of the scheme, the operator is used as the reference, the direction close to the operator is the proximal end, and the direction away from the operator is the distal end.

Figure 2:
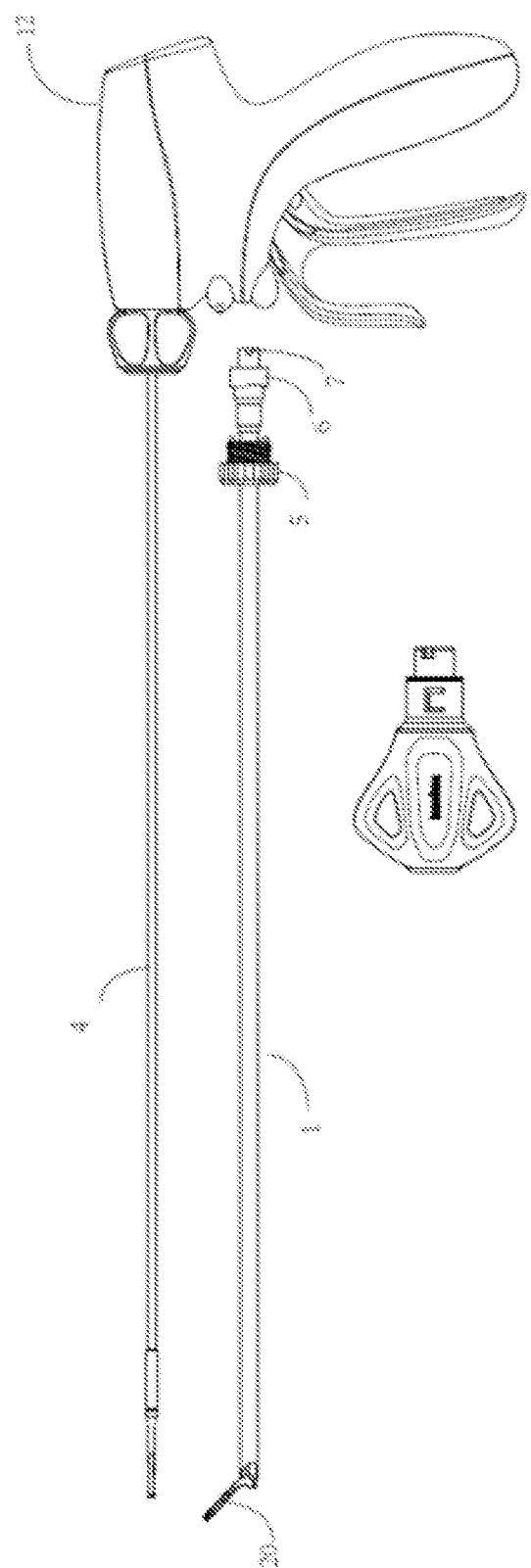
FIG. 2 is an explosive diagram of the sheath assembly of the ultrasonic scalpel of the present invention.
Figure 3:
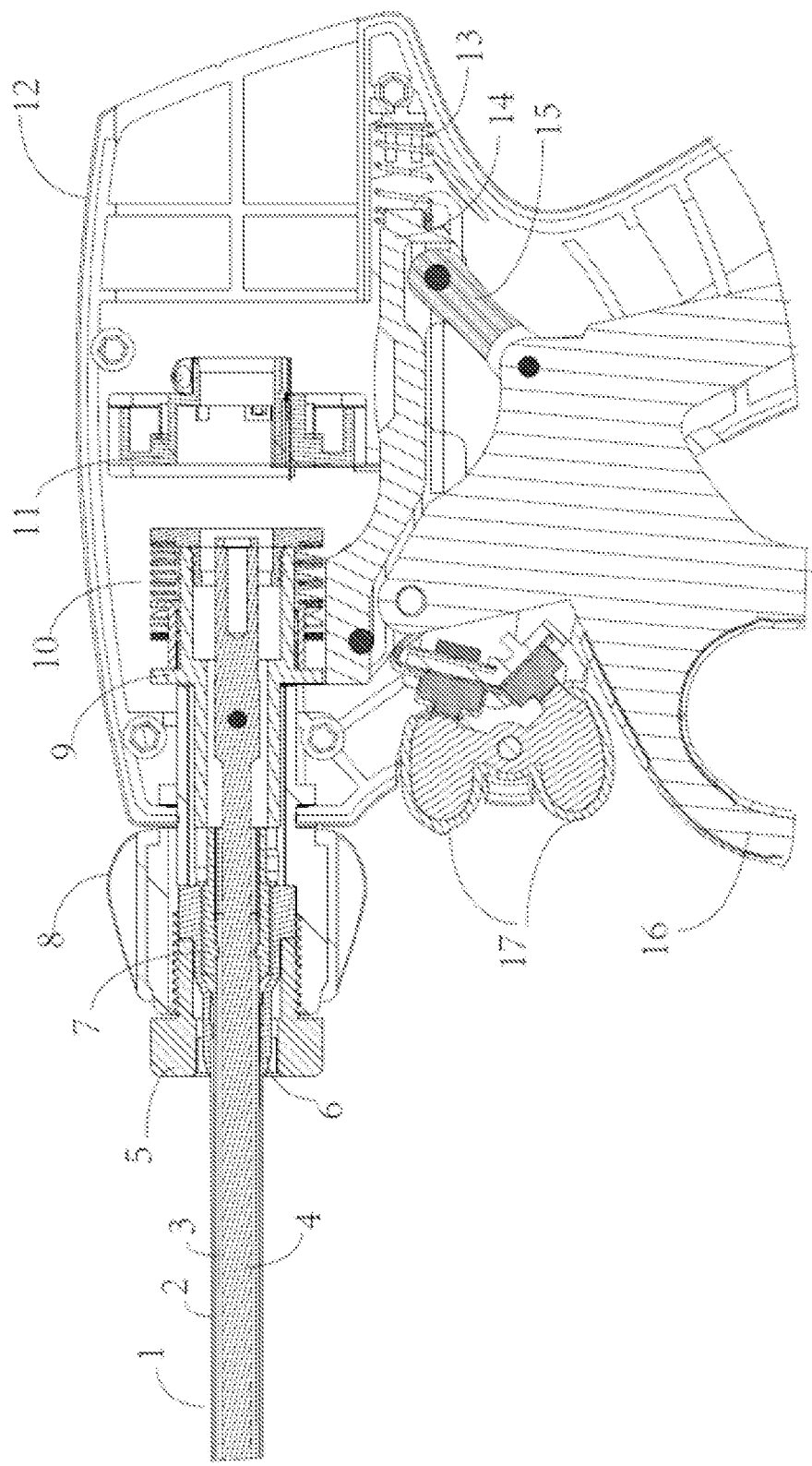
FIG. 3 is a partial cross-section view of the ultrasonic scalpel of the present invention, which shows the connection between the sheath assembly and the handle.
Figure 4:
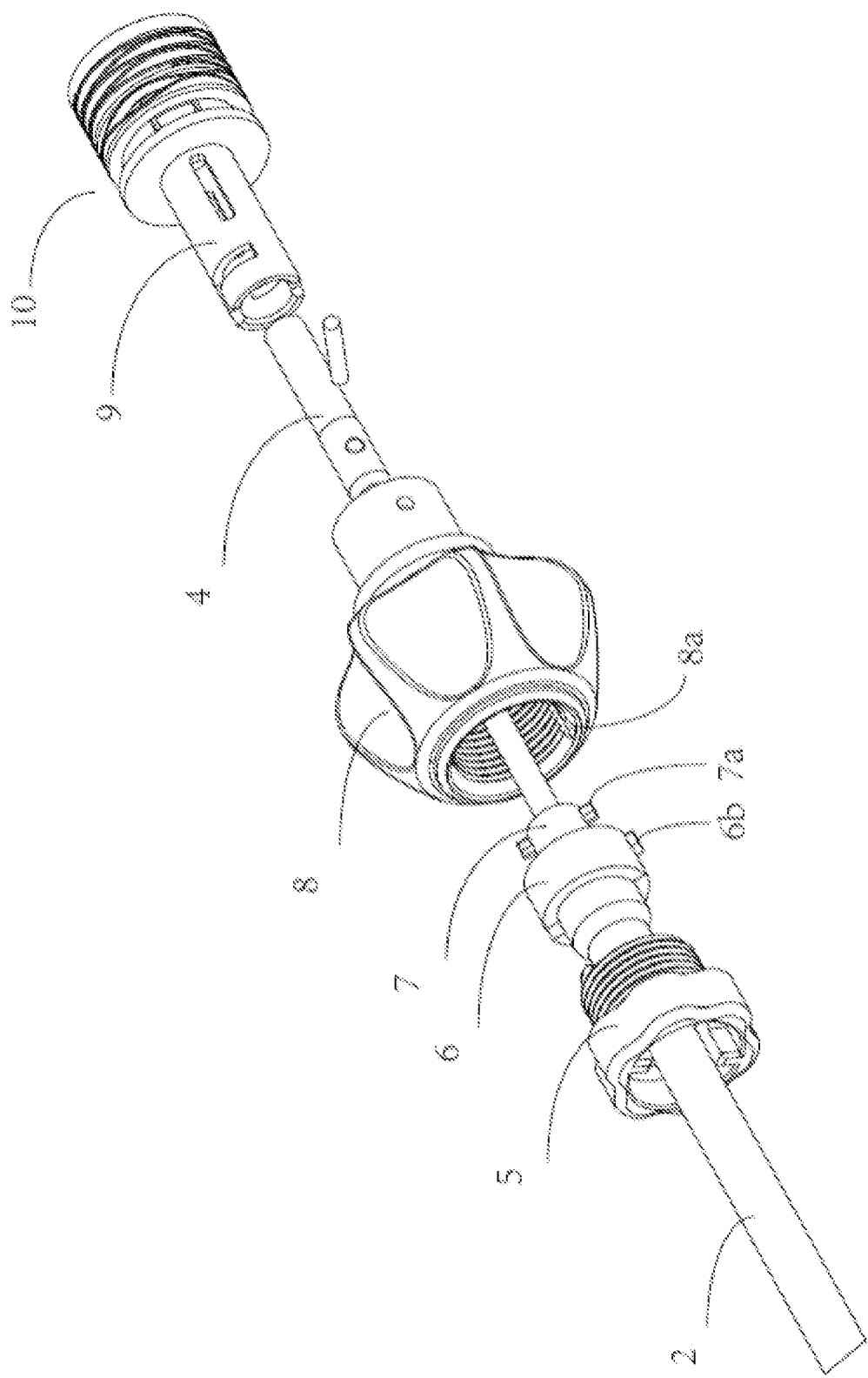
FIG. 4 is an explosive diagram of the connection structure between the sheath assembly and the handle of the ultrasonic scalpel of the present invention.
Figure 5:
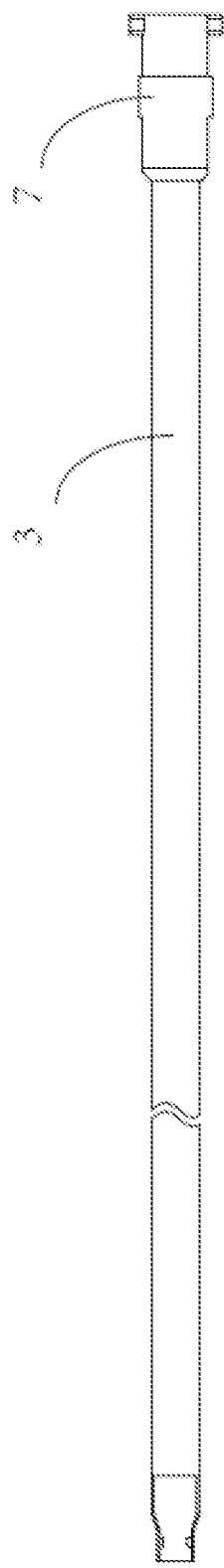
FIG. 5 is a diagram of the structure of the inner sheath assembly of the ultrasonic scalpel of the present invention.
Figure 6:
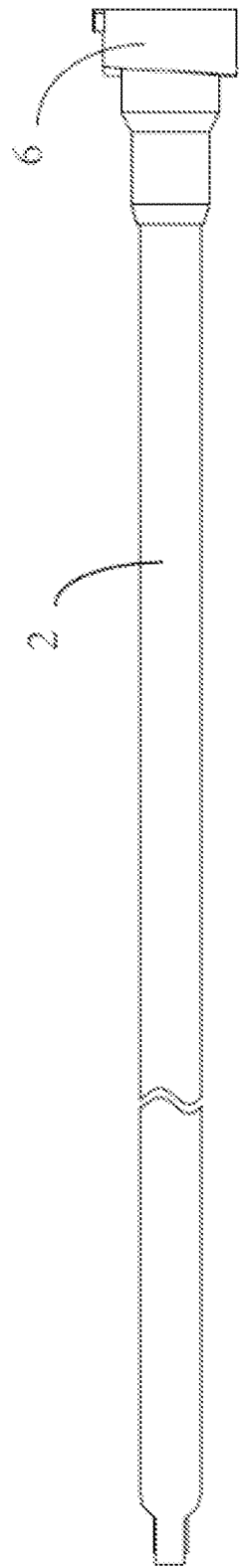
FIG. 6 is a diagram of the structure of the outer sheath assembly of the ultrasonic scalpel of the present invention.
Figure 7:
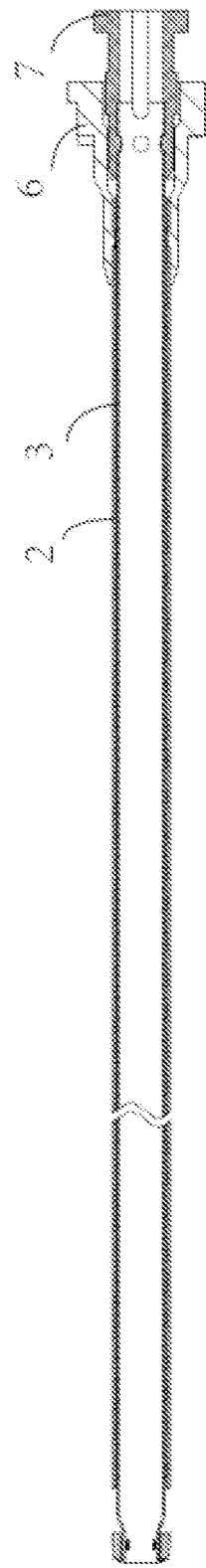
FIG. 7 is a cross-section view of the overall structure of the sheath assembly of the ultrasonic scalpel of the present invention.
Figure 8:
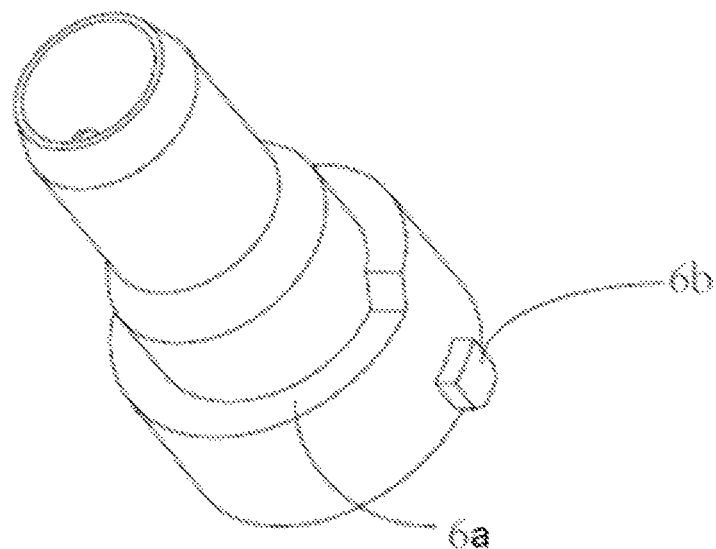
FIG. 8 is a diagram of the outer sheath holder of the ultrasonic scalpel of the present invention.
Figure 9:
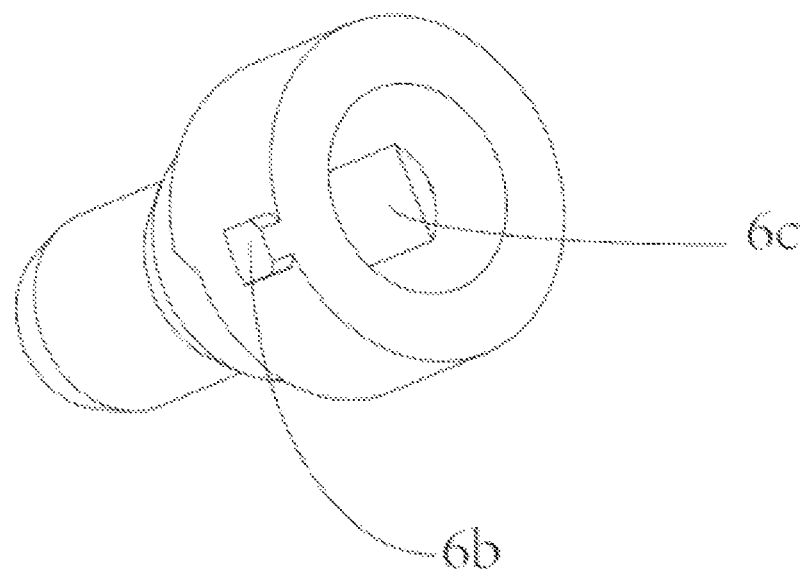
FIG. 9 is a diagram of the outer sheath holder of the ultrasonic scalpel of the present invention in an another orientation.
Figure 10:
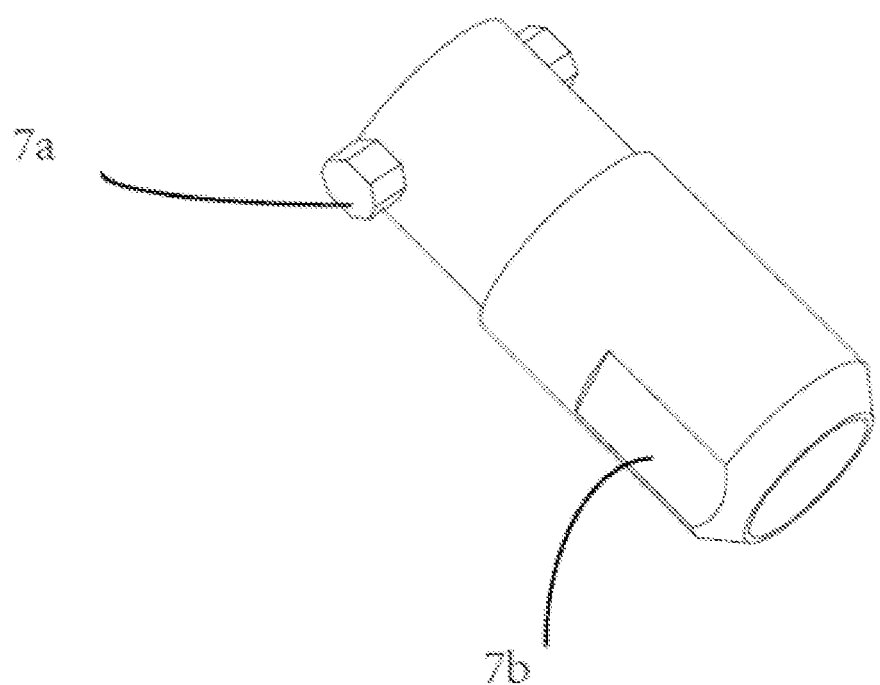
FIG. 10 is diagram of the inner sheath holder of the ultrasonic scalpel of the present invention.
Figure 11:
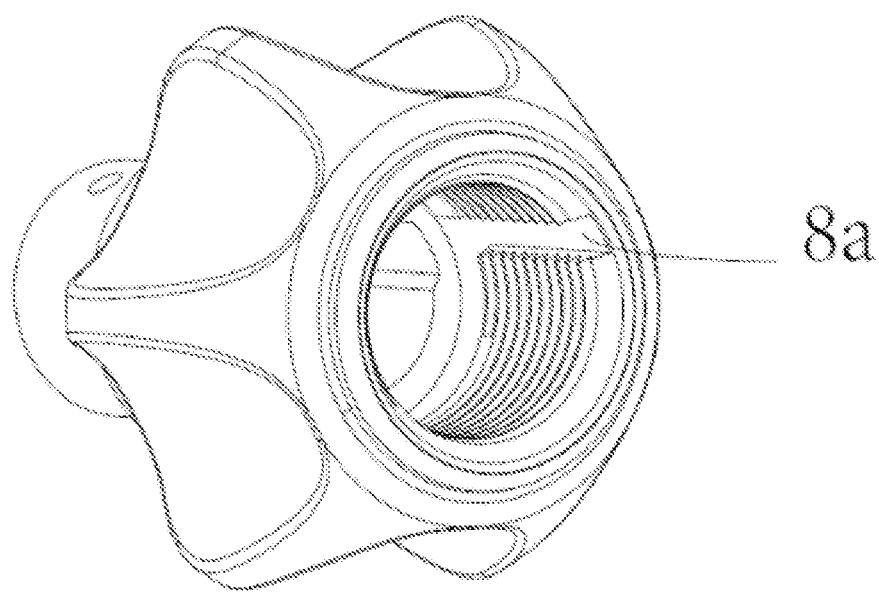
FIG. 11 is a diagram of the tool rotary knob of the ultrasonic scalpel of the present invention.
Figure 12:
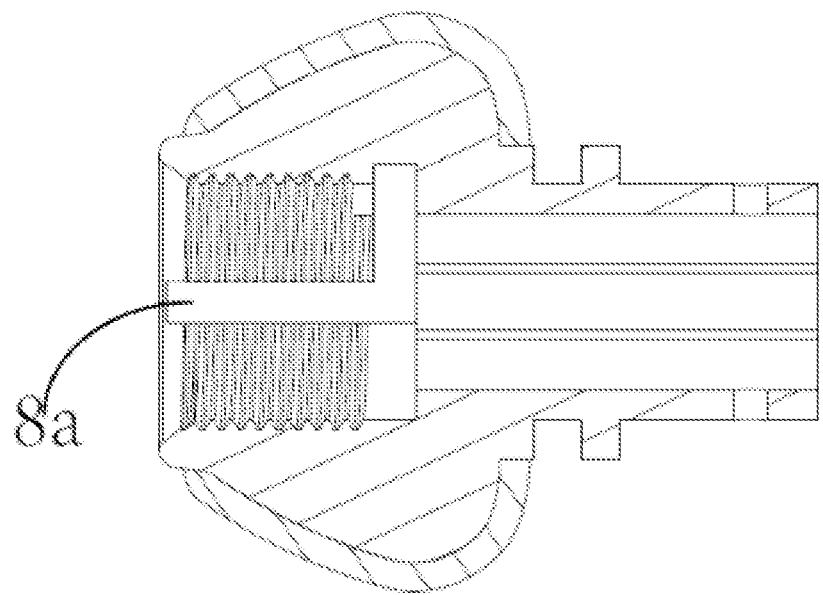
FIG. 12 is a cross-section view of the tool rotary knob of the ultrasonic scalpel of the present invention.

As shown in FIGS. 1 to 3, provided is a reusable ultrasonic scalpel, comprising a handle assembly and an ultrasonic waveguide 4 extended at its distal end for transmitting ultrasonic mechanical energy. Similar to the existing technology, the handle assembly comprises a housing 12, a power touch module set 11 in the housing 12, for the control of ultrasonic energy output, a trigger 16 with its pivot set on the housing 12, and a manual button 17. The trigger 16 through the transmission structure 14, 15 passes force to the spring assembly 10. The manual button 17 is used to trigger the power touch module 11. The housing 12 also includes a reset spring 13 for resetting the transmission structure parts 14 and 15. The specific structure and working principle of the handle assembly are approximately the same as those of existing technology, so this will not be repeated here.

The ultrasonic waveguide 4 outside is equipped with a sheath assembly 1, the sheath assembly 1 is detachably connected to the handle assembly by a quick-connect mechanism. Specifically, the sheath assembly 1 comprises an inner sheath assembly and an outer sheath assembly attached to each other. The inner sheath assembly comprises an inner sheath 3 and an inner sheath holder 7 fixed at its proximal end, and the outer sheath assembly comprises an outer sheath 2 and outer sheath holder 6 fixed at its proximal end. The inner sheath 3 is located between the ultrasonic waveguide 4 and the outer sheath 2, and can move a certain distance along the axis, thus to open or close the active clamp 20, so that the active clamp 20 and the distal end of the waveguide contact or separate.

In combination with FIGS. 5-12, the sheath assembly 1 and the handle assembly have a quick-connect mechanism, which comprises the first quick-connect mechanism and the second quick-connect mechanism. The outer sheath holder 6 is fixed in axial direction by means of the first quick-connect mechanism to the tool rotary knob 8 at the distal end of the handle assembly, while the inner sheath holder 7 is fixed in axial direction by the second quick-connect mechanism to the spring seat 9 arranged within the handle assembly as part of the drive mechanism. The first quick-connect mechanism comprises the first post 6b mounted on the outer perimeter of the proximal end of the outer sheath holder 6, and the L-slot 8a arranged in the rotary knob 8, and they are mated to each other. The second fast-connect mechanism comprises a second post 7a mounted on the outer perimeter of the proximal end of the inner sheath holder 7, and an L-type hook 9a arranged on the spring seat 9, and they are mated to each other.

In general, the first post 6b in the L-slot 8a axial movement distance is equal to the second post 7a in the L-type hook 9a axial movement distance, so that the two can be mated. In practice, the axial movement distance of the first post 6b in the L-slot 8a is slightly longer than the axial movement distance of the second post 7a in the L-type hook 9a, so that the first post 6b of the outer sheath holder 6 can slide first Into the L-slot 8a, play as an axial movement guide. In this technical scheme, it only needs to ensure that the first post 6b and the second post 7a at the same time move axially to the L-slot 8a and the L-type hook 9a until reaching their flat end respectively.

The inner circumferential surface of the outer sheath holder 6 has a first plane 6c, the outer perimeter of the inner sheath holder 7 has a second plane 7b. The outer sheath holder 6 is located over the outer circumference the inner sheath holder 7 and the first plane 6c and the second plane 7b interaction limits the rotation of the inner sheath assembly from the outer sheath assembly, i.e., there will be no relative rotation between the two.

The tool rotary knob 8 comprises an internal thread, with which a sheath mounting knob 5 with an external thread is connected. The proximal end of the sheath mounting knob 5 is facing the outer sheath holder 6 and always exerts a force on it, so that it is fixed between the sheath mounting knob 5 and the tool rotary knob 8. Further, the distal end face of the outer sheath holder 6 there is a step plane 6a, which is to touch with the post 5a at the proximal end of the sheath mounting knob 5.

By combination of FIGS. 4, 13, 14a-14d, and 15a-15c it explains the procedure for assembling or removing the sheath assembly of the ultrasonic scalpel.

Figure 14A:
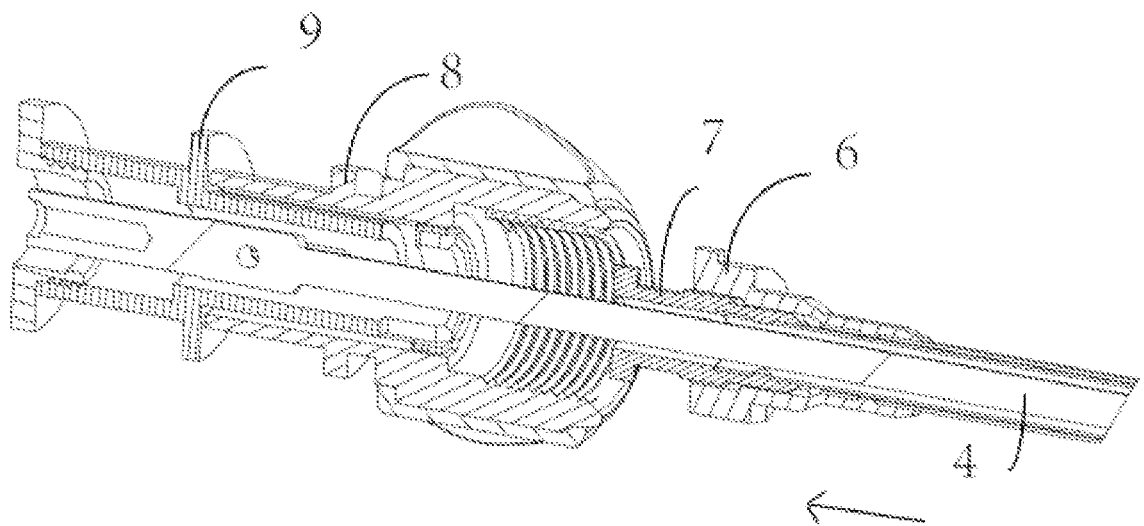
FIGS. 14a-14d are diagrams of the connection between the sheath assembly and the handle of the ultrasonic scalpel of the present invention.

When installing a disposable sheath assembly, the first post 6b of the outer sheath holder 6 is aligned with the L-slot 8a in the tool rotary knob 8, slide into the tool rotary knob 8 in the direction of the arrow of FIG. 14a. Due to The first post 6b on the outer sheath holder 6 has a guiding effect with the L-slot 8a in the tool rotary knob 8, so that the second post 7a on the inner sheath 7 is also aligned with the L-type hook 9a on the spring seat 9.

Figure 14B:
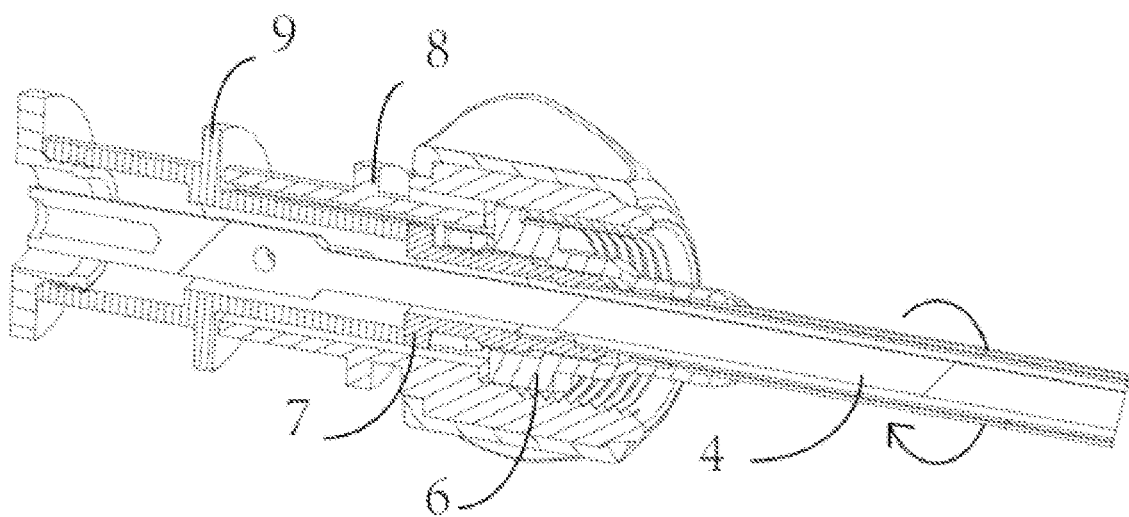
Figure 14C:
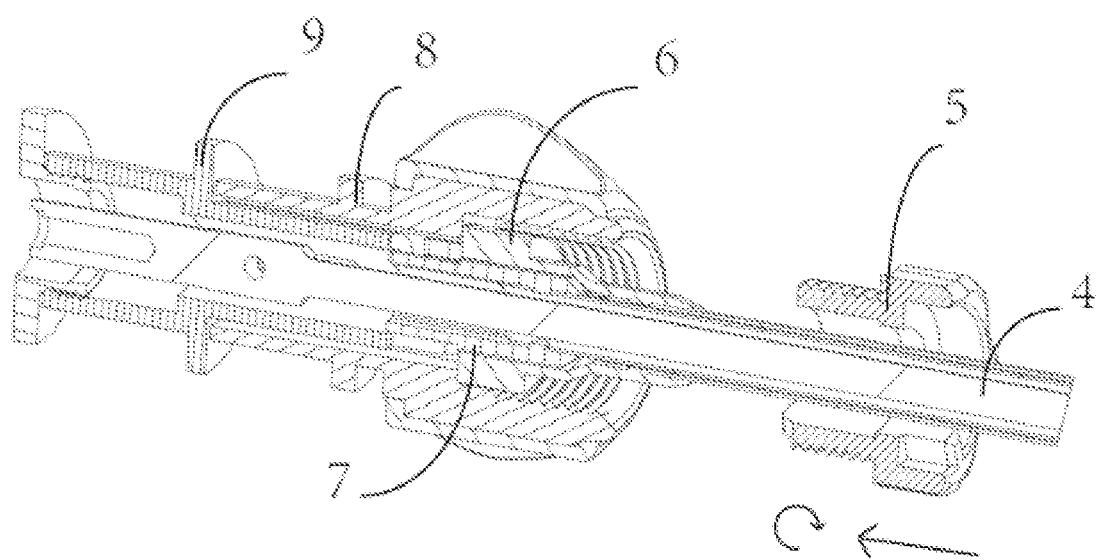
Figure 14D:
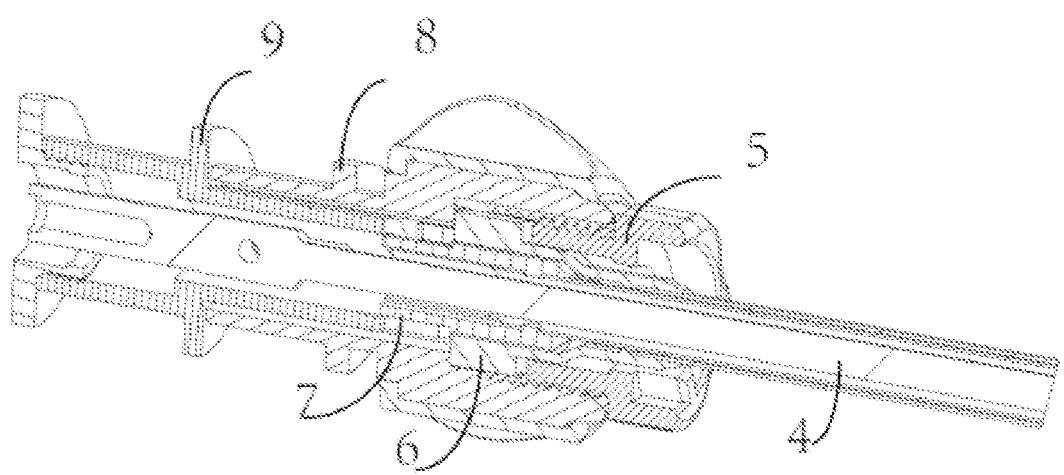

When the disposable sheath assembly slides smoothly to the bottom of the tool rotary knob 8, rotate the sheath assembly in the direction of the arrow shown in FIG. 14b, until the connection between the inner sheath holder 7 and the spring seat 9 and the connection between the outer sheath holder 6 and the tool rotary snob 8 are complete. At this point, the sheath assembly may not be turned to the exact position or has a risk of reversed rotation, so this invention added the sheath installation knob 5, which can make sure the outer sheath holder is installed to the exact position and to prevent the reversal. According to the direction shown in FIG. 14c turn the knob 5 into the tool rotary knob 8. After tightening the sheath assembly, the installation is completed.

Figure 13:
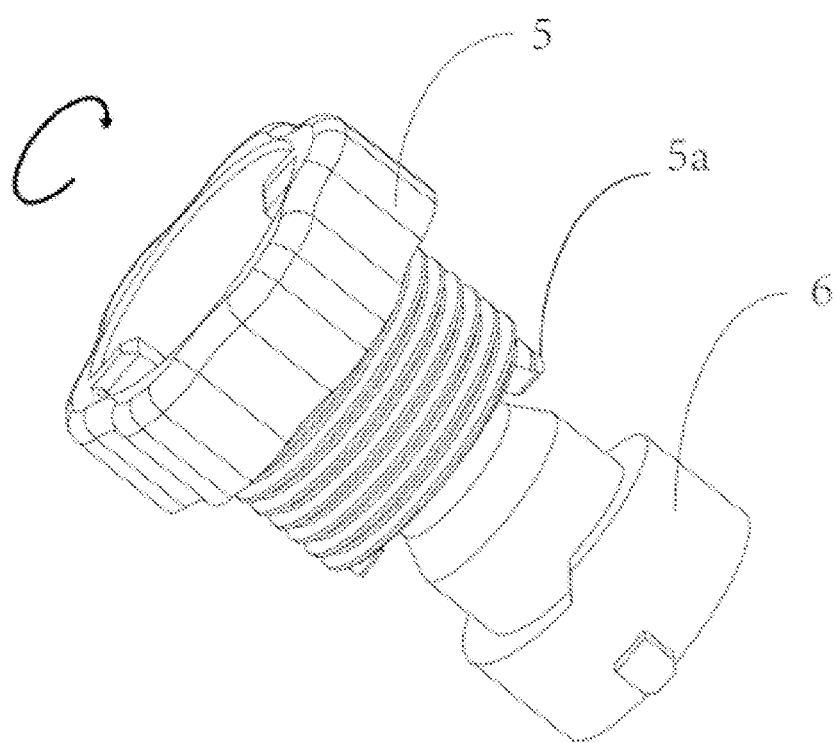
FIG. 13 is an installation diagram of the sheath mounting knob and the outer sheath holder of the ultrasonic scalpel of the present invention.

The principle of preventing reversal is as follows: when assembling a disposable sheath assembly, because the outer sheath holder 6 has a step plane 6a, when the sheath installation knob 5 rotates in the direction shown in FIG. 13, at the end of the sheath installation knob 5 the post 5a contacts the step plane 6a with a certain force, so that the outer sheath holder 6 is subjected to a certain torque. This torque serves two purposes: first, the sheath assembly that is not rotated in place can be rotated to the end of the cross-groove of the L-slot 8a in the tool rotary knob 8, which ensures that the position of the sheath assembly is precise. Second, this torque prevents from loose or reversal. Of course, the step plane 6a can also be a sloped end face with a smooth transition, that is, it only needs a height difference at the distal end surface of the outer sheath holder 6.

Figure 15A:
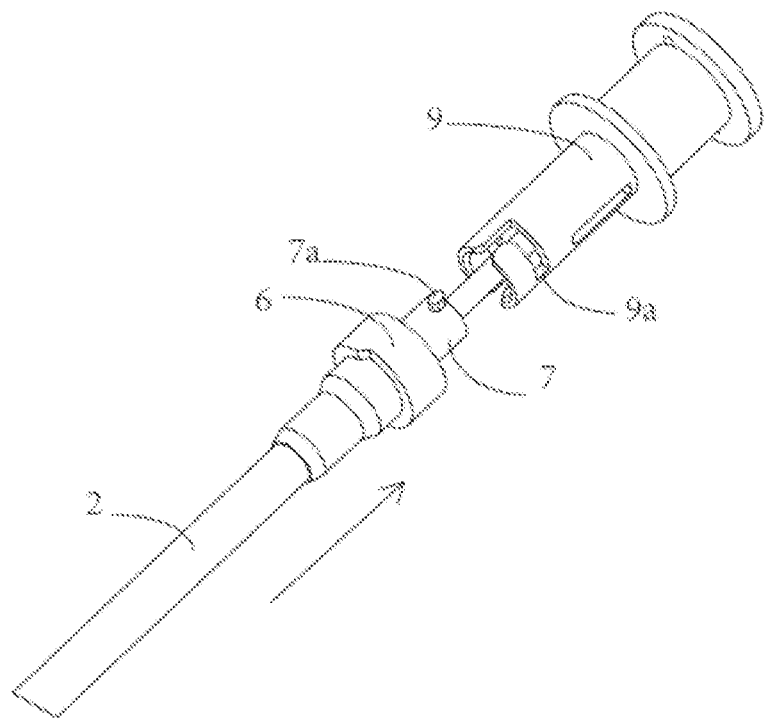
FIGS. 15a-15c are diagrams of the connection between the inner sheath holder and the spring seat of the ultrasonic scalpel of the present invention.
Figure 15B:
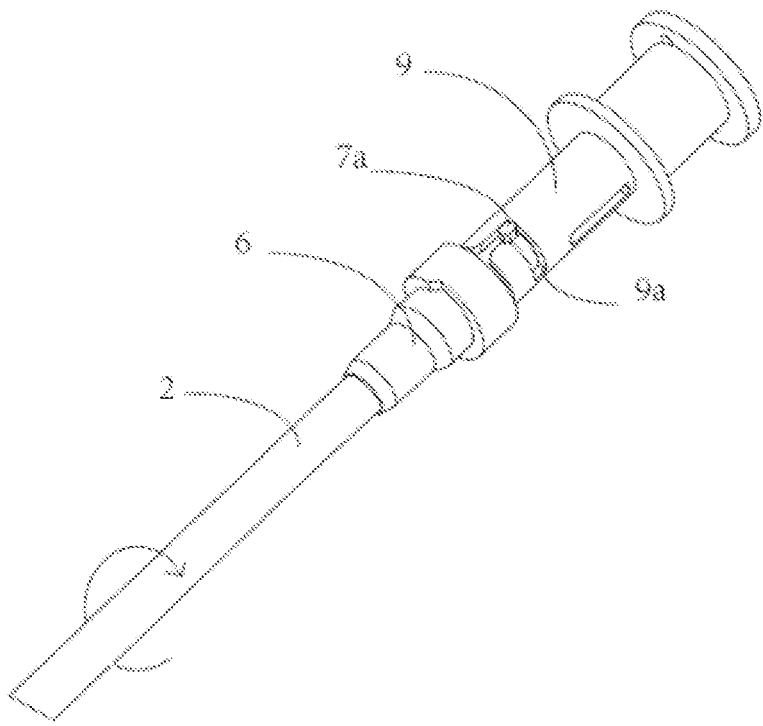
Figure 15C:
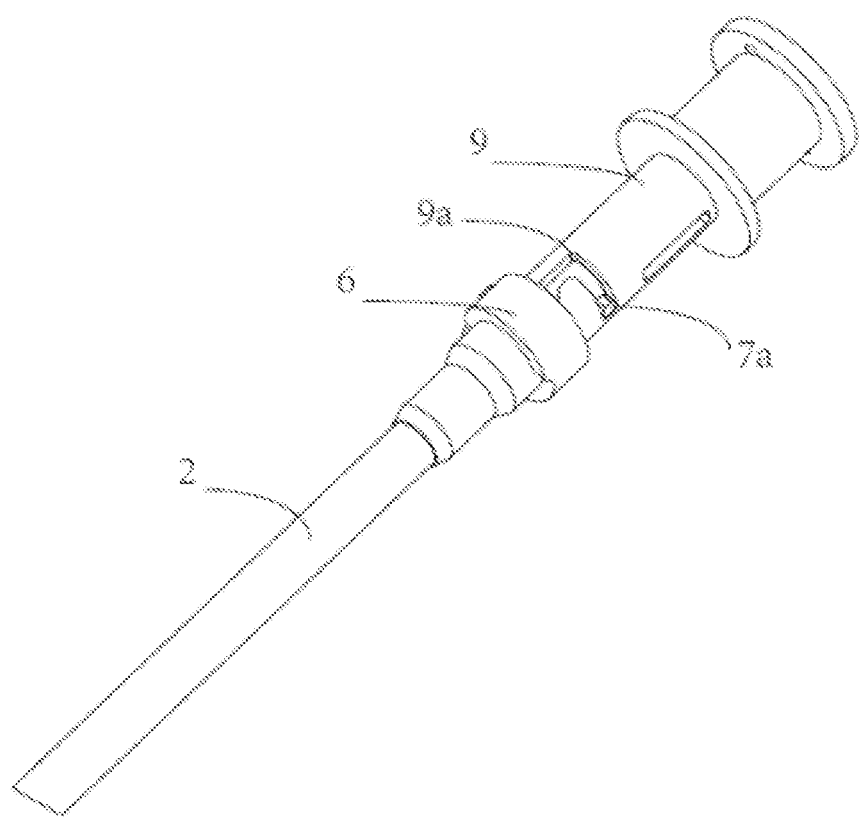

When assembling a disposable sheath assembly, below is the connecting process between the inner sheath holder 7 and the spring seat 9: according to the arrow direction in FIGS. 15a-15c, the second post 7a of the inner sheath holder 7 slides along the L-type hook 9a on the spring seat 9; when sliding to the bottom, rotates according to the direction of the arrow in FIG. 15b, until the second post 7a moves in the L-type hook in the cross-groove, now the inner sheath holder 7 and the spring seat 9 are fixed relatively in the axial motion, so the inner sheath holder 7 and spring seat 9 connection is achieved.

The number of the first post 6b and the second post 7a is not specified. Technical personal in the art should know that 1, 2, or more are possible. The inner sheath 3 and the inner sheath holder 7, the outer sheath 2 and the outer sheath holder 6 are both formed by the mold injection molding process or glue bonding (Insert molding) for making the connecting structure. To make the end connecting structure for the sheath assembly, the conventional tube expanding process causes dimensional instability, and production scrap rate is also high. This invention uses the mold injection molding process or glue bonding, not only can reduce the product scrap rate, but also can make more complex structure to achieve required functions.

The handle assembly and the ultrasonic waveguide 4 are made of high temperature-resistant materials (high-temperature plastic: PPA, PEI, etc.; high-temperature metal: titanium alloy, stainless steel, etc.) and can be cleansed and undergoing high-temperature steam sterilization. Provided is a convenient design for disassembling and assembling, and the user can disassemble and assemble the sheath assembly and the reusable parts in a very short time and easy for hospital use.

The above described is only the preferred embodiment of the present invention, it should be pointed out that the above preferred embodiment shall not be regarded as a limitation to the present invention. The scope of protection of the present invention shall be determined by the scope of the claims. For ordinary technical personnel in the technical field, within the essence and scope of the present invention, can make a number of improvements and modifications, these improvements and modifications should also be regarded as the scope of protection of the present invention.

The invention claimed is:

1. A reusable ultrasonic scalpel, comprising:
   a handle assembly;
   an ultrasonic waveguide extended to a distal end to transmit ultrasonic mechanical energy; and
   a sheath assembly outside a circumference of the ultrasonic waveguide the sheath assembly comprising an inner sheath assembly and an outer sheath assembly attached to each other,
   wherein the inner sheath assembly comprises an inner sheath and an inner sheath holder fixed at a proximal end of the inner sheath,
   wherein the outer sheath assembly comprises an outer sheath and an outer sheath holder fixed at a proximal end of the outer sheath,
   wherein the inner sheath is located between the ultrasonic waveguide and the outer sheath, and is configured to move a particular distance along an axis to open or close an active clamp, so that the active clamp and the distal end of the waveguide contact or separate,
   wherein the inner sheath assembly and outer sheath assembly are fixed in a rotational direction, wherein the sheath assembly is detachably connected to the handle assembly by a first quick-connect mechanism, wherein the outer sheath holder, through the first quick-connect mechanism, is connected to a tool rotary knob at a distal end of the handle assembly and is axially fixed, wherein the inner sheath holder is axially fixed by a second quick-connect mechanism to a spring seat in the handle assembly as part of a drive mechanism, wherein the tool rotary knob comprises an internal thread, wherein a sheath mounting knob with an external thread is connected to the internal thread of the tool rotary knob, wherein a proximal end of the sheath mounting knob is facing the outer sheath holder and exerting a force on the outer sheath holder, so that the outer sheath holder is fixed between the sheath mounting knob and the tool rotary knob, and wherein the external thread of the sheath mounting knob encircles the inner sheath and the outer sheath.

2. The reusable ultrasonic scalpel as described in claim 1 wherein the first quick-connect mechanism comprises a first post mounted on an outer perimeter of the proximal end of the outer sheath holder, and wherein an L-slot is axially arranged within the tool rotary knob, wherein the first post and the L-slot are shaped to mate with each other.

3. The reusable ultrasonic scalpel as described in claim 2 wherein the second quick-connect mechanism comprises a second post mounted on an outer perimeter of the inner sheath and an L-type hook axially arranged on the spring seat, wherein the second post and the L-type hook are shaped to mate with each other.

4. The reusable ultrasonic scalpel as described in claim 3 wherein an axial movement distance of the first post in the L-slot is greater than or equal to an axial movement distance of the second post in the L-type hook.

5. The reusable ultrasonic scalpel as described in claim 1 comprising a first plane on an inner perimeter of the outer sheath holder and a second plane on an outer perimeter of the inner sheath holder, wherein the outer sheath holder is located over an outer circumference of the inner sheath holder and an interaction between the first plane and the second plane limits a rotation of the inner sheath assembly from the outer sheath assembly.

6. The reusable ultrasonic scalpel as described in claim 1 comprising a step plane at a distal end of the outer sheath holder, and a post at the proximal end of the sheath mounting knob that are matched to each other.

7. The reusable ultrasonic scalpel as described in claim 1 wherein the inner sheath and the inner sheath holder are made by injection molding or glue bonding.

8. The reusable ultrasonic scalpel as described in claim 1 wherein the outer sheath and the outer sheath holder are made by injection molding or glue bonding.

9. The reusable ultrasonic scalpel as described in claim 1 wherein the handle assembly and the ultrasonic waveguide are made of high temperature-resistant materials, respectively.

10. A reusable ultrasonic scalpel comprising:
a handle assembly; and
an ultrasonic waveguide extended to a distal end to transmit ultrasonic mechanical energy; and
a sheath assembly around an outside of the ultrasonic waveguide, wherein the sheath assembly comprises an inner sheath assembly and an outer sheath assembly that are attached to each other;
wherein the inner sheath assembly comprises an inner sheath and an inner sheath holder arranged at a proximal end of the inner sheath, wherein the inner sheath and the inner sheath holder are made of plastic material and fixed together by molding or glue;
wherein the outer sheath assembly comprises an outer sheath and an outer sheath holder arranged at a proximal end of the outer sheath, wherein the outer sheath and the outer sheath holder are made of plastic material and are fixed together by molding or glue;
wherein the sheath assembly is detachably connected to the handle assembly by a first quick-connect mechanism,
wherein the outer sheath holder, through the first quick-connect mechanism, is connected to a tool rotary knob at the distal end of the handle assembly and is axially fixed between the tool rotary knob and a sheath mounting knob, and
wherein an external thread of the sheath mounting knob is coupled to an internal thread of the tool rotary knob, the external thread of the sheath mounting knob encircling the inner sheath and the outer sheath.

11. The reusable ultrasonic scalpel described in claim 10 wherein the inner sheath holder is axially fixed by a second quick-connect mechanism to a spring seat, wherein the spring seat is in the handle assembly and is part of a drive mechanism.

* * * * *